(12) United States Patent
Ha

(10) Patent No.: US 7,130,738 B2
(45) Date of Patent: Oct. 31, 2006

(54) METHOD AND APPARATUS FOR MEASURING OIL AERATION OF AN ENGINE

(75) Inventor: Kyoung Pyo Ha, Hwaseong (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 11/169,847

(22) Filed: Jun. 28, 2005

(65) Prior Publication Data

US 2005/0288848 A1    Dec. 29, 2005

(30) Foreign Application Priority Data

Jun. 28, 2004    (KR) .................... 10-2004-0048847

(51) Int. Cl.
  *G01M 15/05*  (2006.01)
  *G01N 33/28*  (2006.01)
(52) U.S. Cl. .................. 701/114; 702/50; 73/19.11
(58) Field of Classification Search .................. None
  See application file for complete search history.

(56) References Cited

U.S. PATENT DOCUMENTS 5,295,083 A * 3/1994 Yano et al. ................. 700/282

6,585,938 B1   7/2003  Machida et al.

FOREIGN PATENT DOCUMENTS

FR          2858056       1/2005
WO       WO 93/08457    4/1993

OTHER PUBLICATIONS

Porot, "Un Nouveau Moyen de Mesure Absolue du Taux Gazeux des Mélanges Gaz-Liquides: Le SMAC," *Revue de L'Institut Francais de Petrole* (1995) 50(6)807:819.
Porot et al., "The SMAC, Under Pressure Oil Aeration Measurement System in Running Engines," SAE International Spring Fuels & Lubricants Meeting, Paris, Jun. 2000.

* cited by examiner

*Primary Examiner*—Andrew M. Dolinar
(74) *Attorney, Agent, or Firm*—Morgan Lewis & Bockius LLP

(57) ABSTRACT

A density $\rho_0$ of pure oil and a density $\rho_a$ of air are calculated based on a measured oil pressure P and a measured oil temperature T of an oil line connecting a hydraulic pump of an engine and an oil gallery of a cylinder block, and then oil aeration is calculated based on a measured oil density $\bar{\rho}$, the measured oil pressure P, the calculated density $\rho_0$ of the pure oil, and the calculated density $\rho_a$ of the air.

11 Claims, 2 Drawing Sheets

METHOD AND APPARATUS FOR MEASURING OIL AERATION OF AN ENGINE

CROSS-REFERENCE TO RELATED APPLICATION

This application claims priority to and the benefit of Korean Patent Application 10-2004-0048847 filed in the Korean Intellectual Property Office on Jun. 28, 2004, the entire content of which is incorporated herein by reference.

BACKGROUND OF THE INVENTION (a) Field of the Invention

The present invention relates to a method and apparatus for measuring oil aeration of an engine. More particularly, the present invention relates to a method and apparatus for measuring oil aeration of a test engine useful for establishing a minimum oil level while designing an engine.

(b) Description of the Related Art

Typically an engine produces a substantial amount of combustion heat and frictional heat during its operation. Therefore, an appropriate supply of oil and coolant must be provided for proper engine operation. For that purpose, an engine is provided with, in its cylinder block and its cylinder head, a lubrication system for oil supply including a hydraulic pump, oil galleries, and oil jets, and a cooling system for coolant supply including components such as a water pump and a water jacket.

The engine oil to be supplied to friction points and operating parts of the engine is stored in an oil pan mounted to the engine at its lower side. The oil stored in the oil pan is drawn by a hydraulic pump in accordance with the engine operation, and is then supplied to each part requiring lubrication through the oil galleries. In that way, the oil circulates through the engine, and it returns to the oil pan when the engine is turned off.

The oil may gradually be lost or degraded by burning in a combustion chamber or leaking out of the engine. Therefore, the amount and state of the engine oil contained in the engine should be periodically checked such that maintenance thereof may be applied when needed.

In an engine test room of a vehicle maker, a minimum oil level that may ensure optimal operation of the engine is established. In order to check the oil level, an engine is traditionally provided with an oil level gauge in the form of a dipstick. Recently, it has become possible to check the oil level electronically.

In order to establish an optimal value of the minimum oil level, oil aeration of a test engine has been measured, and the minimum oil level is established to a value such that the oil aeration might be sufficiently low to provide an oil level above the minimum oil level. However, it is typically required to take the oil from the test engine, and thus real time measurement of the oil aeration is not possible.

The above information disclosed in this Background section is only for enhancement of understanding of the background of the invention and therefore, it may contain information that does not form the prior art that is already known in this country to a person or ordinary skill in the art.

SUMMARY OF THE INVENTION

Embodiments of the present invention provide a method and apparatus for measuring oil aeration of an engine, having advantages including measuring the oil aeration of an engine in real time.

An exemplary apparatus for measuring an oil aeration of an engine according to an embodiment of the present invention includes an oil line connecting a hydraulic pump mounted at the engine and an oil gallery in a cylinder block of the engine, a density sensor mounted on the oil line and measuring oil density of the oil line, a pressure sensor mounted on the oil line and measuring oil pressure of the oil line, a temperature sensor mounted on the oil line and measuring oil temperature of the oil line, and a calculation unit calculating the oil aeration based on the oil density, the oil pressure, and the oil temperature measured by the density sensor, the pressure sensor, and the temperature sensor.

An exemplary method for measuring oil aeration of an engine according to an embodiment of the present invention utilizes a density sensor mounted on an oil line connecting a hydraulic pump of the engine and an oil gallery in a cylinder block and measuring oil density of the oil line, a pressure sensor mounted on the oil line and measuring oil pressure of the oil line, and a temperature sensor mounted on the oil line and measuring oil temperature of the oil line. The exemplary method includes measuring oil density $\bar{\rho}$ of the oil line using the density sensor, measuring oil pressure P of the oil line using the pressure sensor, measuring oil temperature T of the oil line using the temperature sensor, calculating a density $\rho_0$ of pure oil based on the measured oil pressure P and the measured oil temperature T, calculating a density $\rho_a$ of air based on the measured oil pressure P and the measured oil temperature T, and calculating oil aeration $\Psi$ based on the measured oil density $\bar{\rho}$, the measured oil pressure P, the calculated density $\rho_0$ of the pure oil, and the calculated density $\rho_a$ of the air.

In a further embodiment, the oil density $\rho_0$ is calculated by the equation $\rho_0(P,T)=\rho_0(P_0,T_0)+\gamma\Delta P-\beta\Delta T$ based on the measured oil pressure P, the measured oil temperature T, an oil density $\rho_0(P_0,T_0)$ at a predetermined temperature $T_0$ and a predetermined pressure $P_0$, a thermal expansion coefficient $\beta$ of the pure oil, a compression ratio $\gamma$ of the pure oil, and a gas constant R of the air.

In a further embodiment, the density $\rho_a$ of the air is calculated by the equation $$\rho_a = \frac{P}{RT}$$

based on the measured oil pressure P, the measured oil temperature T, and the gas constant R of the air.

In a further embodiment, the oil aeration $\Psi$ is calculated by the equation $$\Psi = \frac{1}{1+\left(\frac{P_{atm}}{P}\right)^{\frac{1}{\gamma}}\left(\frac{\bar{\rho}-\rho_a}{\rho_0-\bar{\rho}}\right)}$$

based on the measured oil density $\bar{\rho}$, the measured oil pressure P, the calculated density $\rho_0$ of the pure oil, and the calculated density $\rho_a$ of the air.

DETAILED DESCRIPTION OF THE EMBODIMENTS

An embodiment of the present invention will hereinafter be described in detail with reference to the accompanying drawings.

Figure 1:
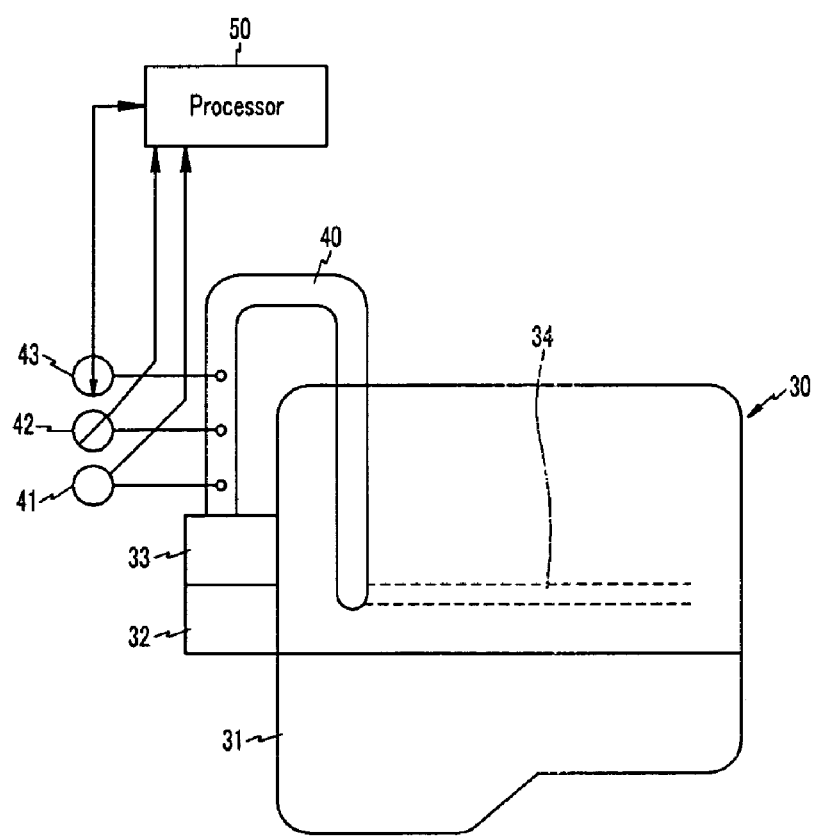
FIG. 1 is a schematic diagram of an apparatus for measuring oil aeration of an engine according to an exemplary embodiment of the present invention.
Figure 2:
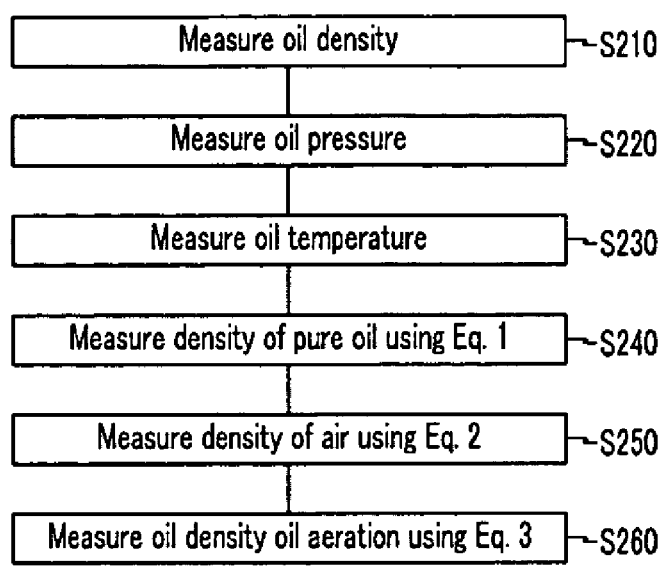
FIG. 2 is a flowchart showing a method for measuring oil aeration of an engine according to an exemplary embodiment of the present invention.

Referring first to FIG. 1, an apparatus for measuring oil aeration of an engine according to an exemplary embodiment of the present invention is applied to a test engine 30, and the test engine 30 is provided with an oil line 40 used for measuring oil aeration. The test engine 30 is an engine used for determining a minimum oil level in designing a practical engine. The test engine 30 is provided with the same lubrication system as a practical engine, including an oil pan 31, a hydraulic pump 32, an oil filter 33, an oil gallery 34, etc.

Additionally, exterior to the test engine 30, an oil line 40 is formed at the oil filter 33 such that devices for testing the oil pumped by the hydraulic pump 32 may be mounted. It is not necessary for the oil line 40 to be exteriorly exposed, and the oil line may be formed inside of the engine provided that the devices may be mounted thereon. The oil line 40 is mounted with a density sensor 41 for measuring oil density, a pressure sensor 42 for measuring oil pressure, and a temperature sensor 43 for measuring oil temperature.

In addition, a calculation unit 50 calculates the oil aeration of the oil based on the oil density, the oil pressure, and the oil temperature measured from the density sensor 41, the pressure sensor 42, and the temperature sensor 43. The calculation unit 50 may be realized as at least one microprocessor programmed with a predetermined program, and the predetermined program may include a set of instructions for performing a method according to an exemplary embodiment of the present invention. Associated hardware and software for execution of calculation unit 50 may be selected and programmed by a person of ordinary skill in the art based on the teachings contained herein.

The oil density $\bar{\rho}$, oil pressure P, and oil temperature T respectively measured by the sensors 41, 42, and 43 are used for obtaining the oil aeration $\Psi$.

The measured values $\bar{\rho}$, P, and T are applied to the following Equations 1 to 3, together with the density $\rho_0(P_{atm}, 0)$ of pure oil at 0° C. and atmospheric pressure, a thermal expansion coefficient $\beta$ of the pure oil, a compression ratio $\gamma$ of the pure oil, and a gas constant R of an air.

$$\rho_0(P,T) = \rho_0(P_0, T_0) + \gamma \Delta P - \beta \Delta T \quad \text{(Equation 1)}$$

Equation 1 is an equation for obtaining the density $\rho_0(P,T)$ of the pure oil at the measured oil pressure P and the measured oil temperature T.

In the above Equation 1, $\gamma$ denotes the compression ratio of the pure oil, and $\beta$ denotes a thermal expansion coefficient of the pure oil. The compression ratio $\gamma$ of the pure oil and the thermal expansion coefficient $\beta$ of the pure oil may have different values depending on the oil.

Also, in the above Equation 1, $\rho_0(P_0, T_0)$ denotes the density of the pure oil at a predetermined temperature $T_0$ and a predetermined pressure $P_0$. For example, according to an exemplary embodiment of the present invention, 0° C. is used for the predetermined temperature $T_0$, and atmospheric pressure (i.e., 1 bar) is used for the predetermined pressure $P_0$.

Also in the above Equation 1, $\Delta P$ denotes a difference $P - P_0$ between the measured oil pressure P and the predetermined pressure $P_0$.

Also in the above Equation 1, $\Delta T$ denotes a difference $T - T_0$ between the measured oil temperature T and the predetermined temperature $T_0$.

The density $\rho_0(P,T)$ of the pure oil at the measured oil pressure P and the measured oil temperature T may be calculated by Equation 1 for the following reasons.

Oil density depends on temperature and pressure. Therefore, when the oil density is known at a reference temperature and a reference pressure, the oil density at an actually measured temperature and pressure may be obtained by expecting a density change according to a temperature change and a density change according to a pressure change.

The thermal expansion coefficient $\beta$ of the oil is used for obtaining a density change according to the temperature change, and the compression ratio $\gamma$ of the oil is used for obtaining a density change according to the pressure change.

$$\rho_a = \frac{P}{RT} \quad \text{(Equation 2)}$$

Equation 2 is an equation for obtaining the density $\rho_a$ of air at the measured oil pressure P and the measured oil temperature T.

In the above Equation 2, R denotes a gas constant of the air.

The aerated oil and the air are at equilibrium, and therefore, it may be presumed that the temperatures and pressures thereof are the same. According to Equation 2, the density of the air at the measured oil pressure P and the measured oil temperature T is obtained by using an ideal gas equation, upon the above presumption.

$$\Psi = \frac{1}{1 + \left(\frac{P_{atm}}{P}\right)^{\frac{1}{\gamma}} \left(\frac{\bar{\rho} - \rho_a}{\rho_0 - \bar{\rho}}\right)} \quad \text{(Equation 3)}$$

Equation 3 is an equation for obtaining oil aeration $\Psi$ from the measured oil pressure P, the measured oil temperature T, and the measured oil density $\bar{\rho}$, with the use of the density $\rho_0(P,T)$ of the pure oil and the density $\rho_a$ of the air obtained according to Equations 1 and 2.

In the above Equation 3, $P_{atm}$ denotes atmospheric pressure.

The oil aeration $\Psi$ is defined as a volumetric ratio of the air in the aerated oil. Therefore, Equation 3 may be derived from the definitions of the oil aeration $\Psi$ and other parameters included in Equation 3.

The oil aeration $\Psi$ at a specific temperature T and pressure P may be obtained from Equations 1–3 as follows.

That is, from the measured oil density $\bar{\rho}$, pressure P, and temperature T respectively measured by the sensors 41, 42, and 43 on the oil line 40, oil aeration $\Psi$ of the test engine may be measured using constant values in Equations 1–3 in the following steps.

Firstly, through steps S210, S220, and S230, the oil density $\bar{\rho}$, the oil pressure P, and the oil temperature T are respectively measured by the density sensor 41, the pressure sensor 42, and the temperature sensor 43.

Subsequently at step S240, such obtained oil pressure P, temperature T, oil density $\rho_0(P_{atm}, 0)$ at 0° C. and atmospheric pressure, thermal expansion coefficient β, compression ratio γ, and gas constant R of the air are substituted into Equation 1 so as to calculate the density $\rho_0$ of the pure oil.

Subsequently at step S250, the density $\rho_a$ of pure air is calculated by Equation 2 using the oil pressure P and temperature T obtained through the steps S210–S230 and the gas constant R of the air.

Subsequently at step S260, the aeration Ψ of the oil is calculated by Equation 3 using the oil density $\bar{\rho}$, oil pressure P, density $\rho_0$ of the pure oil, and air density $\rho_a$ obtained through S210–250.

Therefore, a minimum oil level of an engine may be determined based on such obtained oil aeration Ψ. That is, the oil aeration Ψ of the test engine 30 is obtained in the test room as the amount of oil contained in the test engine 30 is varied.

A minimum amount of the oil at which the oil aeration Ψ satisfies a predetermined standard may be determined as the minimum oil level of the engine.

As described above, according to an embodiment of the present invention, the oil aeration of a test engine is easily obtained at various oil levels in real time and accordingly the minimum oil level may be determined efficiently.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for measuring oil aeration of an engine, comprising:
   an oil line connecting a hydraulic pump mounted at the engine and an oil gallery in a cylinder block of the engine;
   a density sensor mounted on the oil line and measuring oil density of the oil line;
   a pressure sensor mounted on the oil line and measuring oil pressure of the oil line;
   a temperature sensor mounted on the oil line and measuring oil temperature of the oil line; and
   a calculation unit calculating the oil aeration based on the oil density, the oil pressure, and the oil temperature respectively measured by the density sensor, the pressure sensor, and the temperature sensor, wherein said calculation unit is programmed to execute instructions for:
   calculating density $\rho_0$ of pure oil based on measured oil pressure P and measured oil temperature T;
   calculating density $\rho_a$ of air based on measured oil pressure P and measured oil temperature T; and
   calculating oil aeration Ψ based on the measured oil density $\bar{\rho}$, measured oil pressure P, the calculated density $\rho_0$ of pure oil, and the calculated density $\rho_a$ of air;
   wherein the calculation unit is further programmed to calculate the oil density $\rho_0$ as $\rho_0(P,T)=\rho_0(P_0,T_0)+\gamma\Delta P-\beta\Delta T$, where in $\rho_0(P_0,T_0)$ is the oil density at a predetermined temperature $T_0$ and a predetermined pressure $P_0$, β is a thermal expansion coefficient of pure oil, and γ is a compression ratio of pure oil and a gas constant R of air.

2. The apparatus of claim 1, wherein the calculator unit is further programmed to calculate the density $\rho_0$ of air as $$\rho_a = \frac{P}{RT},$$

wherein R is a gas constant of air.

3. The apparatus of claim 1, wherein the calculation unit is further programmed to calculate the oil aeration Ψ as $$\Psi = \frac{1}{1+\left(\frac{P_{atm}}{P}\right)^{\frac{1}{\gamma}}\left(\frac{\bar{\rho}-\rho_a}{\rho_0-\bar{\rho}}\right)}$$

wherein $P_{atm}$ is atmospheric pressure.

4. The apparatus of claim 1, wherein the calculation unit is programmed to calculate:
   the density $\rho_0$ of the air as $$\rho_a = \frac{P}{RT};$$

the oil aeration Ψ as $$\Psi = \frac{1}{1+\left(\frac{P_{atm}}{P}\right)^{\frac{1}{\gamma}}\left(\frac{\bar{\rho}-\rho_a}{\rho_0-\bar{\rho}}\right)}$$

wherein $P_{atm}$ is atmospheric pressure.

5. A method for measuring oil aeration of an engine with the use of a density sensor mounted on an oil line connecting a hydraulic pump of the engine and an oil gallery in a cylinder block and measuring oil density of the oil line, a pressure sensor mounted on the oil line and measuring oil pressure of the oil line, and a temperature sensor mounted on the oil line and measuring oil temperature of the oil line, the method comprising:
   measuring oil density $\bar{\rho}$ of the oil line using the density sensor;
   measuring oil pressure P of the oil line using the pressure sensor;
   measuring oil temperature T of the oil line using the temperature sensor;
   calculating density $\rho_0$ of pure oil based on the measured oil pressure P and the measured oil temperature T;
   calculating density $\rho_a$ of air based on the measured oil pressure P and the measured oil temperature T; and
   calculating oil aeration Ψ based on the measured oil density $\bar{\rho}$, the measured oil pressure P, the calculated density $\rho_0$ of pure oil, and the calculated density $\rho_a$ of the air;
   wherein the oil density $\rho_0$ is calculated by the equation $\rho_0(P,T)=\rho_0(P_0,T_0)+\gamma\Delta P-\beta\Delta T$ based on the measured oil temperature T, oil density $\rho_0(P_0,T_0)$ at a predetermined temperature $T_0$ and a predetermined pressure $P_0$, a thermal expansion coefficient β of the pure oil, and a compression ratio γ of pure oil and a gas constant R of air.

6. The method of claim 5, wherein the density $\rho_a$ of the air is calculated by the equation $$\rho_a = \frac{P}{RT}$$

based on the measured oil pressure P, the measured oil temperature T, and a gas constant R of air.

7. The method of claim 5, wherein the oil aeration Ψ is calculated by the equation $$\Psi = \frac{1}{1 + \left(\frac{P_{atm}}{P}\right)^{\frac{1}{\gamma}}\left(\frac{\overline{\rho} - \rho_a}{\rho_0 - \overline{\rho}}\right)}$$

based on the measured oil density $\overline{\rho}$, the measured oil pressure P, the calculated density $\rho_0$ of the pure oil, the calculated density $\rho_a$ of the air, and atmospheric pressure $P_{atm}$.

8. The method of claim 5, wherein:

the density $\rho_a$ of the air is calculated by the equation $$\rho_a = \frac{P}{RT}$$

based on the measured oil pressure P, the measured oil temperature T, and the gas constant R of air;

the oil aeration Ψ is calculated by the equation $$\Psi = \frac{1}{1 + \left(\frac{P_{atm}}{P}\right)^{\frac{1}{\gamma}}\left(\frac{\overline{\rho} - \rho_a}{\rho_0 - \overline{\rho}}\right)}$$

based on the measured oil density $\overline{\rho}$, the measured oil pressure P, the calculated density $\rho_0$ of the pure oil, and the calculated density $\rho_a$ of the air, and atmospheric pressure $P_{atm}$.

9. A method for measuring oil aeration of an engine, comprising:

measuring oil density of oil supplied to the engine;
measuring oil pressure of oil supplied to the engine;
measuring oil temperature of oil supplied to the engine;
calculating density of pure oil based on the measured oil pressure and the measured oil temperature;
calculating density of air based on the measured oil pressure and the measured oil temperature; and
calculating oil aeration based on the measured oil density, the measured oil pressure, the calculated density of pure oil, and the calculated density of air;
wherein the oil density is calculated at a predetermined temperature and a predetermined pressure, based on a thermal expansion coefficient of pure oil, and a compression ratio of pure oil and a gas constant of air.

10. The method of claim 9, wherein the density of air is calculated based on a ratio between the measured oil pressure, and the measured oil temperature and a gas constant of air.

11. The method of claim 9, wherein the oil aeration is calculated based on a relationship between the measured oil density, the measured oil pressure, the calculated density of pure oil, and the calculated density of air.

* * * * *